United States Patent [19]
Lekholm

[11] Patent Number: 5,824,885
[45] Date of Patent: Oct. 20, 1998

[54] METHOD INTENDED FOR USE IN ANAESTHETIC SYSTEMS FOR IDENTIFYING ANAESTHETICS

[75] Inventor: Anders Lekholm, Bromma, Sweden

[73] Assignee: Siemens Elema AB, Solna, Sweden

[21] Appl. No.: 591,158

[22] Filed: Jan. 25, 1996

[30] Foreign Application Priority Data

Feb. 14, 1995 [SE] Sweden .................................. 9500530

[51] Int. Cl.⁶ .............................. G01N 9/12; G01N 25/18
[52] U.S. Cl. ............................. 73/53.01; 73/440; 73/444; 73/448; 128/203.12; 374/44
[58] Field of Search .................... 73/53.01, 433, 73/437, 440, 444, 448; 374/44; 128/203.12

[56] References Cited

U.S. PATENT DOCUMENTS

| | | | |
|---|---|---|---|
| 576,537 | 2/1897 | Barry | 73/444 |
| 1,937,755 | 12/1933 | Ginger et al. | 73/444 |
| 2,078,977 | 5/1937 | Samiran | 73/448 |
| 2,320,720 | 6/1943 | Croft . | |
| 4,825,860 | 5/1989 | Falb et al. | 128/203.12 |
| 5,157,968 | 10/1992 | Zfira | 73/433 X |
| 5,272,907 | 12/1993 | Hakala . | |
| 5,348,394 | 9/1994 | Hori et al. . | |

FOREIGN PATENT DOCUMENTS

| | | | |
|---|---|---|---|
| 0 247 789 | 12/1987 | European Pat. Off. . | |
| 37 15 495 | 8/1988 | Germany . | |
| 202863 | 11/1983 | Japan | 374/44 |
| 86818 | 3/1994 | Japan . | |
| 2008650 | 2/1994 | Russian Federation | 73/440 |
| 1827609 | 7/1993 | U.S.S.R. | 374/44 |
| 4088 | 8/1913 | United Kingdom | 73/448 |
| 1343309 | 1/1974 | United Kingdom | 73/440 |
| 2 240 849 | 2/1990 | United Kingdom . | |
| WO 84/03878 | 10/1984 | WIPO . | |

OTHER PUBLICATIONS

Lienert, "Konstitutive Ein flüsse auf die Schallgeschwindigkeit", Wien–tierärztl. Mschr., vol. 62, No. 6, Aug. 1975, pp. 235–240.

Primary Examiner—Hezron E. Williams
Assistant Examiner—Daniel S. Larkin
Attorney, Agent, or Firm—Hill, Steadman & Simpson

[57] ABSTRACT

In order to keep a patient from being administered an incorrect anaesthetic, an erroneous concentration of an anaesthetic or a mixture of anaesthetics, an anaesthetic system can be equipped with a device for identifying anaesthetics in anaesthetic system. The device identifies anaesthetics by determining a parameter related to a physical property, such as density, of liquid anaesthetics. A floating body can be immersed in the anaesthetic fluid. The floating body then sinks to a depth which depends on the fluid's density. The identity of the anaesthetic can then be read off a measurement stick arranged on the floating body.

15 Claims, 6 Drawing Sheets

5,824,885

METHOD INTENDED FOR USE IN ANAESTHETIC SYSTEMS FOR IDENTIFYING ANAESTHETICS

BACKGROUND OF THE INVENTION

1. Field of the Invention

The present invention relates to a method and a device for identifying at least one anaesthetic in an anaesthetic system.

2. Description of the Prior Art

In general, placing a patient in a state of anaesthesia, or narcosis, means that the patient is rendered unconscious and unable to feel any pain. Usually, a mixture of oxygen, nitrous oxide, an anaesthetic gas and possibly air is supplied to the patient via a breathing circuit in an anaesthetic system. The most common anaesthetic gases are halothane, desflurane, enflurane, isoflurane and sevoflurane. The anaesthetic is normally in a liquid state in an anaesthetic vaporizer in the anaesthetic system and a desired amount of anaesthetic gas is vaporized from the liquid and delivered to the breathing circuit as anaesthesia is induced in the patient.

Different anaesthetics, which are administered in different concentrations, have different effects on the patient. The side-effects of different anaesthetics also differ. Anaesthetic systems are thus available which can be equipped with a number of anaesthetic vaporizers enabling the anaesthetist to choose the anaesthetic he or she deems best for the patient, without any need to connect or detach different anaesthetic vaporizers during surgery. This may be the case e.g. in surgery on children or in an operation of long duration.

A mixture of different anaesthetics, however, should not be supplied to the patient, since the effect of such a mixture is unpredictable and largely unknown. The anaesthetic system, therefore, must be devised so that only one anaesthetic at a time can be supplied to the patient. It is possible, however, that a number of anaesthetic gases could become mixed, even in an anaesthetic system which utilizes only one anaesthetic vaporizer, such as when the active anaesthetic vaporizer is filled with anaesthetic.

In order to minimize the risk of errors in the administration of anaesthetics, it would be advantageous if the anaesthetic system were capable of automatically identifying the anaesthetic administered to the patient. With such a capability, the anaesthetic system then could be devised to stop the supply of anaesthetic to the patient, if an error occurs, and simultaneously warn staff of the error.

As noted above, the different known anaesthetics can be supplied to the patient in different concentrations. If an incorrect concentration is set for a particular anaesthetic, the patient could be subjected to needless risks, i.e. an overdosage or underdosage of the anaesthetic. This would also be the case if an incorrect anaesthetic were supplied.

These risks also would be greatly reduced if the anaesthetic could be identified before being supplied to the patient.

In the field of anaesthesia, the identification of anaesthetic with optical methods is known, i.e., using absorption spectrometry. Since many anaesthetics have a similar absorption spectrum, absorption must be measured at a number of different wavelengths in order to make a distinguishing identification. This makes expensive, complex equipment necessary for identifying anaesthetics. Optical measurements are generally performed on the gas mixture supplied to the patient, i.e., with the anaesthetic in a gaseous state.

Another known way of identifying an anaesthetic is based on the use and combination of two different measurement methods for determining the concentration of the anaesthetic as well as for identifying the anaesthetic. An optical method could be used for measuring the anaesthetic at a specific wavelength, and measurement could be made with an oscillating crystal coated with a layer of oil or grease which absorbs and resorbs the anaesthetic gas. Depending on the molecular weight and concentration of the anaesthetic, the crystal's oscillation frequency changes to varying degrees. A combination of these two measurement methods yields a unique signal for every known anaesthetic. It should be noted that measurement using changes in crystal frequency only, is not in itself sufficient for identifying anaesthetics, since the frequency change is identical for the different anaesthetics at the concentrations in which they are used. One such device is described in U.S. Pat. No. 5,272,907.

SUMMARY OF THE INVENTION

An object of the present invention is to provide a device for identifying an anaesthetic in an anaesthetic system in a simple and reliable manner.

This object is achieved in accordance with the invention in a device having at least one container, which can be filled with the anaesthetic in liquid form, and a measurement unit for determining at least one parameter related to at least one physical property, preferably one or more of the physical properties density, sound velocity, viscosity, thermal conductivity, surface tension, thermal absorption and solubility, of the anaesthetic fluid in the container, thereby identifying the anaesthetic.

One advantage of the device according to the invention is that determination of the anaesthetic is performed while the anaesthetic is still in the liquid state. There is then no risk of administering the wrong anaesthetic, a mixture of anaesthetics, or the wrong concentration of an anaesthetic (provided the concentration of the gas mixture supplied to the patient is measured simultaneously) to the patient. Performing a determination or identification by determining a physical property of the anaesthetic fluid would also be advantageous. In this context, "physical property" refers to a property related to the fluid itself, such as density, viscosity, thermal conductivity etc. Combined measurement of two physical properties would yield more reliable identification in instances in which two anaesthetics have very similar properties. One way to increase reliability in the identification of anaesthetics from a physical property is to perform a simultaneous check on, or measurement of, the temperature of the anaesthetic fluid, since a number of the cited physical properties are temperature-related.

In an embodiment of the device according to the invention the measurement unit contains a density-sensitive means for determining a parameter related to the density of the anaesthetic fluid at a known temperature.

Different anaesthetics have different densities (see Table 1 below). An anaesthetic can be identified when a parameter, directly related to density, is determined. There are several ways in which such a parameter can be determined. Since identification of the anaesthetic is made while the anaesthetic is still in the liquid state, administration of an incorrect anaesthetic can be stopped before the anaesthetic has been vaporized. Alternatively, the concentration in vaporized anaesthetic can be automatically adjusted, so the patient is not administered a concentration which is too high or too low. The anaesthetic system can be devised so the physician selects the desired anaesthetic in some appropriate manner, and the device automatically checks that the correct anaesthetic is actually present in the anaesthetic vaporizer activated during surgery.

TABLE 1

Density of anaesthetic in the liquid state at 20° C.

| Anaesthetic | Density [kg/m3]- |
| --- | --- |
| Halothane | 1,868 |
| Enflurane | 1,523 |
| Isoflurane | 1,502 |
| Sevoflurane | 1,520 |
| Desflurane | 1,465 |

One way of obtaining a parameter is achieved in accordance with the invention in an embodiment wherein the density-sensitive means comprises a floating body immersed in the anaesthetic fluid, the floating body sinking to a specific depth below the surface of the fluid, said depth depending on the density of the anaesthetic fluid at the known temperature.

Since the floating body sinks to different depths, depending on the density of the anaesthetic fluid, staff can visually identify the anaesthetic fluid quickly and simply. The parameter in this instance is therefore specific depth. When the temperature is well-known, the difference in density between the different anaesthetics is sufficient to cause specific depth to vary to such a degree that visual identification is simple. As table 1 above shows, enflurane and sevoflurane are closest to each other. The difference is 3 kg/m3, which is the same as 3 mg/ml. This difference is big enough for the floating body's specific depth to vary on the order of 1 cm. The position of the floating body can also be automatically read with an appropriate sensor, preferably an optical sensor.

In this embodiment, preferably the floating body settles in the anaesthetic fluid in a position with a given side up and a measuring stick is arranged on the given side to indicate the identity of the anaesthetic at the surface of the fluid. The density of the measuring stick is advantageously selected at a value corresponding to the density of the anaesthetic agents. As noted above, variations in specific depth are relatively large, even for anaesthetics with the most similar densities. To keep the measuring stick from being too long, when adapted to all anaesthetics, at least two floating bodies can be arranged at a predetermined distance from each other on the measuring stick. One of the floating bodies would then correspond to a particular length of the measuring stick, which could therefore be made much shorter.

A second way of obtaining a parameter is achieved in accordance with the invention in an embodiment wherein the density-sensitive means comprises a predetermined number of floating elements, placed in the container, the density of a first floating element being the same as the density of a first anaesthetic, the density of a second floating element being the same as the density of a second anaesthetic etc., so different floating elements float or sink according to the anaesthetic in the container.

This design is mainly based on the same principle as the first embodiment. Instead of measuring density and identifying the anaesthetic, the design uses floating elements adapted to different anaesthetic densities, and identification is made on the basis thereof. With the use of floating elements, devised to float or sink depending on the anaesthetic, identification can be performed more simply. Automatic identification is also facilitated by this design.

Preferably the container has a cylindrical cavity for each floating element, the cavities being devised so the floating elements can be in an upper part or a lower part of the cavities. When the cavities are filled with anaesthetic fluid, a transparent window is arranged on either side of the container in the upper part and lower part of the cavities respectively, enabling light to pass through the windows and cavities when no floating element is opposite the windows. A light source is arranged at each window on one side of the container to emit light through the respective window. A light detector is arranged at each window on the other side of the container to sense whether any light passes through the window and the container and an identification unit is connected to the light sources and light detectors. The identification unit identifies an anaesthetic fluid in the cavities from the windows blocked by a floating element.

Since the floating elements float or sink in different anaesthetic fluids, a unique signal combination is obtained from the light detectors for each anaesthetic. This enables the device to automatically determine the identity of the anaesthetic present in the anaesthetic system, and the anaesthetic system can accordingly be devised to automatically stop the vaporization of an anaesthetic and/or sound an alarm if the anaesthetist sets an incorrect anaesthetic or an incorrect concentration of the sensed anaesthetic.

A third way of obtaining a parameter is achieved in accordance with the invention in an embodiment wherein the container is filled with a predetermined amount of anaesthetic fluid, and the density-sensitive means comprises a weight-sensing element, connected to the container, to sense a relative or absolute container weight when the container is filled with anaesthetic fluid, and an identification unit which identifies the anaesthetic from the sensed weight.

The mass, or weight, of a given amount of anaesthetic fluid corresponds to the density of the fluid and can therefore be used as a parameter for direct identification of the anaesthetic. The weight-sensing element can be devised in a number of different ways, depending on the amount of anaesthetic fluid which is to be weighed. In weighing e.g. 1 ml, the sensitivity of the weight-sensing element must be less than 3 mg.

Irrespective of the parameter the device is designed to sense, it is advantageous to arrange a thermostat to regulate the anaesthetic fluid's temperature, so the fluid is maintained at a constant, predetermined temperature. A separate thermometer and algorithms for calculating the density for different anaesthetic fluids at a measured temperature are thereby unnecessary.

Some anaesthetic vaporizers are occasionally devised for a specific anaesthetic, e.g. halothane. In these instances, the device can be specifically devised to identify this anaesthetic. Merely checking whether the right anaesthetic is present may be sufficient in some instances. Knowing that the anaesthetic vaporizer contains the incorrect anaesthetic is sufficient for the physician. The identity of the incorrect anaesthetic is then irrelevant.

If two anaesthetic fluids are accidentally mixed in a vaporizer, the density changes to an erroneous value. This error would be discovered by the device according to the invention, even if the incorrect anaesthetic is not identified.

DESCRIPTION OF THE PREFERRED EMBODIMENTS

Figure 1:
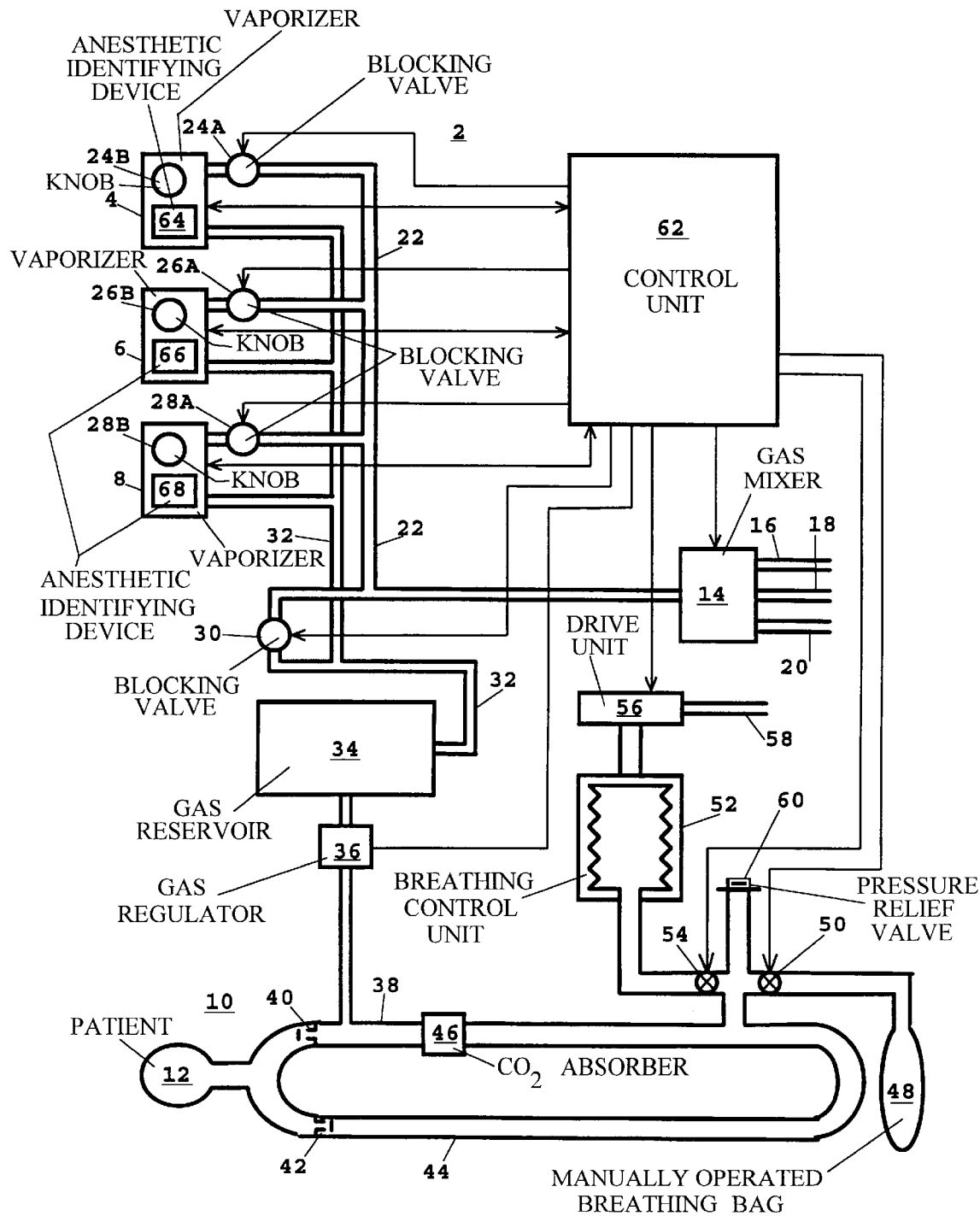
FIG. 1 shows the basic components of a known anaesthetic system.

FIG. 1 shows anaesthetic system 2 to which a first anaesthetic vaporizer 4, a second anaesthetic vaporizer 6 and a third anaesthetic vaporizer 8 are attached for selectively supplying an anaesthetic to a respiratory circuit 10. The respiratory circuit 10 then delivers a respiratory gas containing anaesthetic gas to a patient 12.

The respiratory gas is supplied to the anaesthetic system 2 via first gas mixer 14. Gas can be carried to the first gas mixer 14 via a first gas connection 16, a second gas connection 18 and a third gas connection 20. The supplied gases can consist of air, nitrous oxide and oxygen. If only oxygen and nitrous oxide are to be supplied to the anaesthetic system 2, the third gas connection 20 can either be kept closed or also used for supplying oxygen. Supplying oxygen via two separate gas connections enhances patient safety. The incoming gases are mixed in the gas mixer 14 in selectable proportions to form a respiratory gas with a specific pressure, a predetermined flow of the mixed respiratory gas then being carried through a first gas line 22 to the anaesthetic vaporizers 4, 6 and 8.

A first blocking valve 24A is arranged by the first anaesthetic vaporizer 4. The first blocking valve 24A, which is normally closed, keeps gas from the first gas line 22 from passing through the first anaesthetic vaporizer 4. When a first setting knob 24B on the first anaesthetic vaporizer 4 is activated by an operator, the first blocking valve 24A opens, and anaesthetic fluid in the first anaesthetic vaporizer 4 is vaporized in order to produce the selected concentration of anaesthetic in the breathing gas. In the corresponding manner, a second blocking valve 26A is arranged by the second anaesthetic vaporizer 6, and a third blocking valve 28A is arranged by the third anaesthetic vaporizer 8. The second blocking valve 26A opens when a second setting knob 26B is activated, and the third blocking valve 28A opens when a third setting knob 28B on the third anaesthetic vaporizer 8 is activated. The three blocking valves 24A, 26A and 26C are regulated so only one can be activated at a time.

A fourth blocking valve 30 is arranged by the first gas line 22 to pass a flow of gas which has not passed through any of the anaesthetic vaporizers 4, 6 and 8.

The anaesthetic system 2 is devised so the fourth blocking valve 30 automatically opens if the first blocking valve 24A, the second blocking valve 26A and the third blocking valve 28A are closed. This ensures that the patient is supplied with respiratory gas in every situation.

Respiratory gas from the gas mixer 14 then passes, with or without anaesthetic gas, through a second gas line 32 to a gas reservoir 34. The respiratory gas is further mixed in the gas reservoir 34, so vaporized anaesthetic is mixed with respiratory gas as thoroughly as possible before being sent to the respiratory circuit 10.

In this instance, the respiratory circuit 10 consists of a recirculating respiratory circuit in which the patient 12 re-breathes a greater or lesser part of the gas in the respiratory circuit 10. Here, the ready-mixed respiratory gas in the gas reservoir 34 can suitably be referred to as fresh gas for the respiratory circuit 10. Fresh gas is supplied to the respiratory circuit 10 to compensate for gas losses, or gas releases, from the respiratory circuit 10, e.g. by the uptake of oxygen and anaesthetic gas by the patient 12 and leakage in the entire circuit system (the respiratory circuit 10 and the patient 12).

The supply of fresh gas to the respiratory circuit 10 is regulated in a fresh gas regulator 36. Fresh gas is carried to an inspiratory line 38 in the respiratory circuit 10 and delivered to the patient 12 through a first check valve 40. Expired gas is carried from the patient through a second check valve 42 and an expiratory line 44. A carbon dioxide absorber 46 is also arranged in the respiratory circuit 10.

Two possible drive systems for respiratory gas in the respiratory circuit 10 are designated in FIG. 1. The first is a manually squeezed breathing bag 48 which, via a valve 50, can be connected to the respiratory circuit 10. When the breathing bag 48 is connected to the respiratory circuit 10, a doctor can manually squeeze the breathing bag 48 to control inspiration and expiration of the patient 12. Alternatively, a breathing control unit 52, consisting of a bellows in a container, which can be connected to the respiratory circuit via a valve 54, can mechanically act on the gas in the respiratory circuit 10. Regulation of the breathing control unit 52 is provided by a drive unit 56 which, using compressed air from a fourth gas connection 58, can send a drive gas to the breathing control unit 52 and divert drive gas from same. Surplus gas in the respiratory circuit bleeds off through a pressure relief valve 60.

The anaesthetic system 2 is controlled and monitored by a control unit 62. The control unit 62 therefore regulates the operation of the gas mixer 14, drive unit 56, fresh gas regulator 36, blocking valves 24A, 26A, 28A, 30 and anaesthetic vaporizers 4, 6, 8. The control unit 62 also receives the functional information, set by staff, on e.g. breathing rate, the desired tidal volume, the composition of the respiratory gas etc. The other functions of the control unit 62 will be apparent from the following.

In order to identify the anaesthetics connected to the anaesthetic system 2, each of the anaesthetic vaporizers 4, 6 and 8 has a device 64, 66, and 68 for identifying the anaesthetic in the respective anaesthetic vaporizer 4, 6, or 8. Information on the anaesthetic in the respective anaesthetic vaporizer 4, 6, or 8 is sent to the control unit 62.

A number of versions of the devices 64, 66 and 68 are possible. Three embodiments, designated 64, 66 and 68, are described below.

Figure 2A:
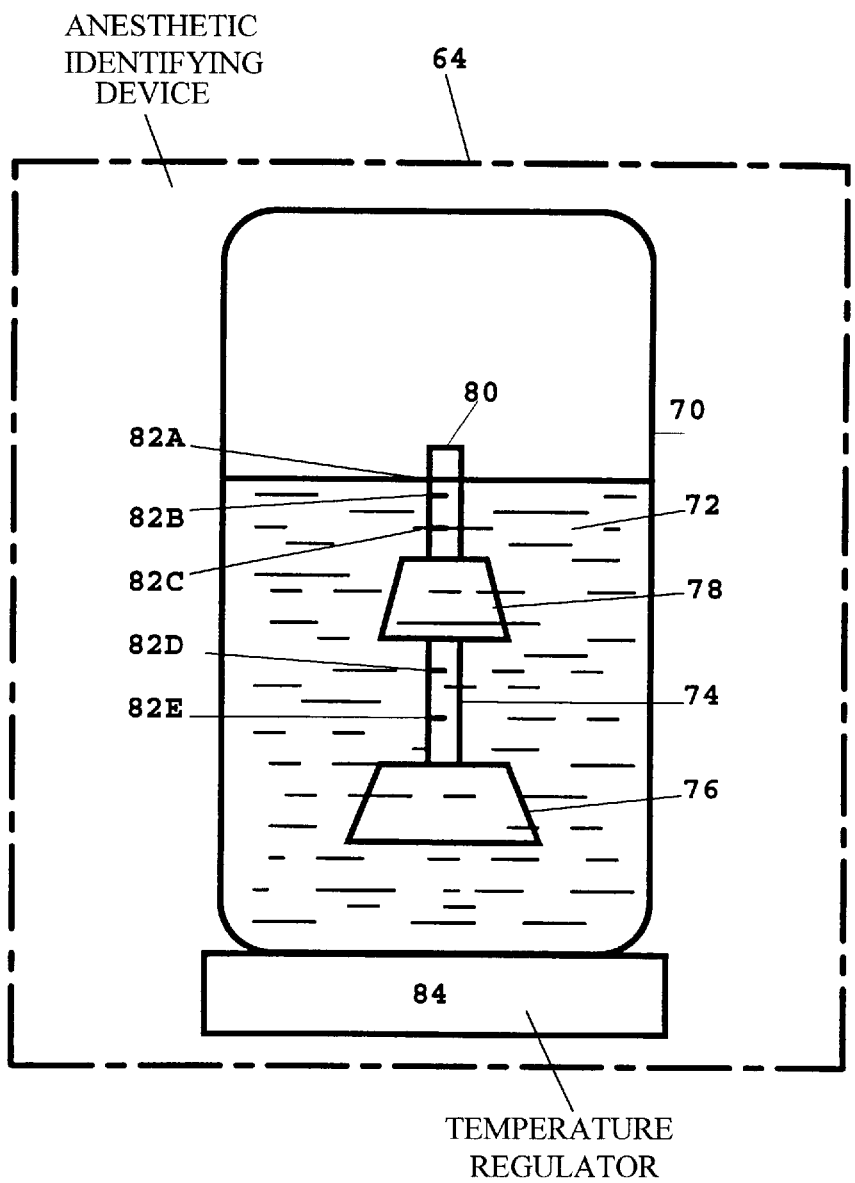
FIGS. 2A and 2B show a first embodiment of an anaesthetic identifying device constructed according to the invention.
Figure 2B:
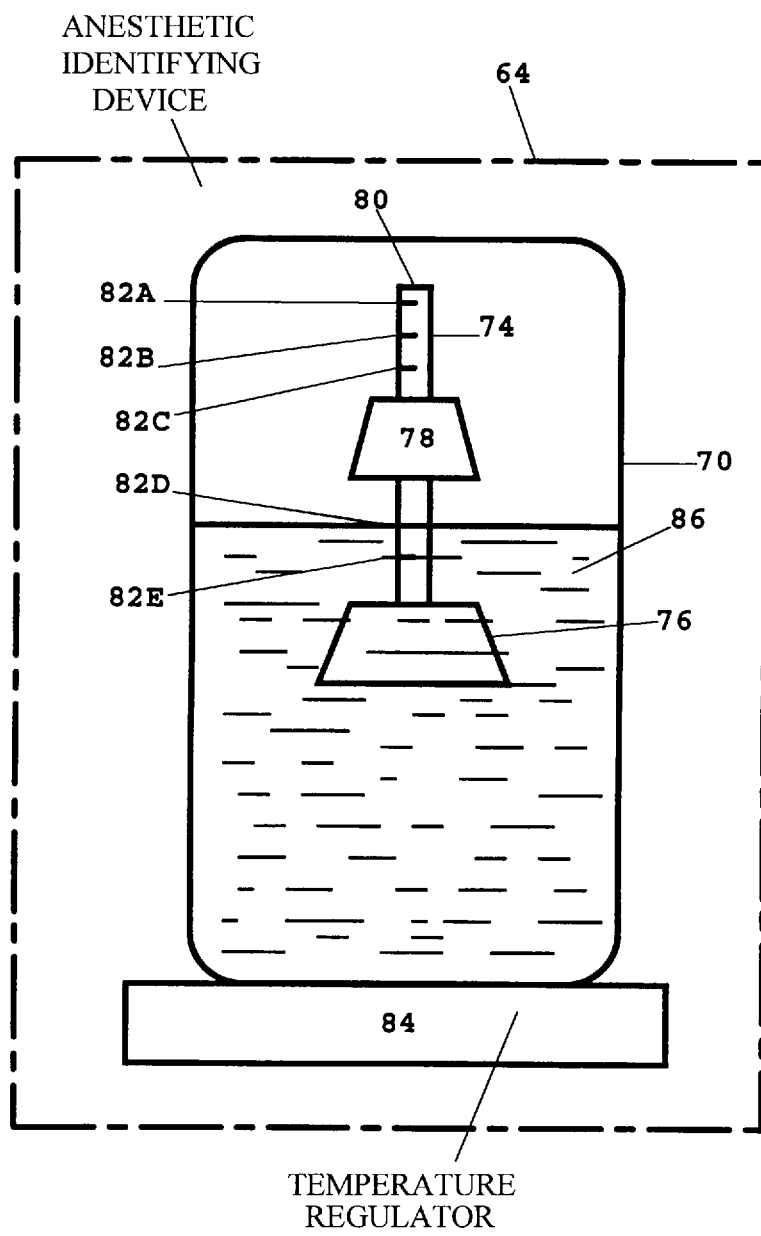

FIGS. 2A and 2B show a first embodiment of the device 64. The anaesthetic vaporizer 4 contains a container 70 for an anaesthetic fluid 72. A floating body 74 is immersed in the anaesthetic fluid 72. The floating body 74 is devised to float at different depths, depending on the density of the anaesthetic fluid 72. Here, the floating body 74 consists of a first floating body part 76, a second floating body part 78 and a measuring stick 80. The second floating body part 78 makes it possible for the measuring stick 80 to be shorter. The measuring stick 80 has different markings 82A–82E. Each of these markings 82A–82E corresponds to a specific anaesthetic, and the marking 82A–82E at the surface of the fluid designates the density of the anaesthetic fluid 72 in which the floating body 74 is immersed.

The temperature of the anaesthetic fluid 72 is regulated by a temperature regulator 84, but the fluid can alternatively contain a thermometer which measures the temperature. If the anaesthetic vaporizer is filled with some other anaesthetic by mistake, the floating body will shift from its specific position and, depending on the degree of mixture, move to a greater or lesser degree away from the markings 82A–82E.

FIG. 2A shows the position of the floating body 74 for one anaesthetic fluid 72, and FIG. 2B shows the position of the floating body 74 for another anaesthetic fluid 86.

The first embodiment of the device 64 is based on external visual identification by staff. In principle, an optical reader or the like can also be arranged in the device 64 to read the anaesthetic's identity on the measuring stick 78.

Figure 3A:
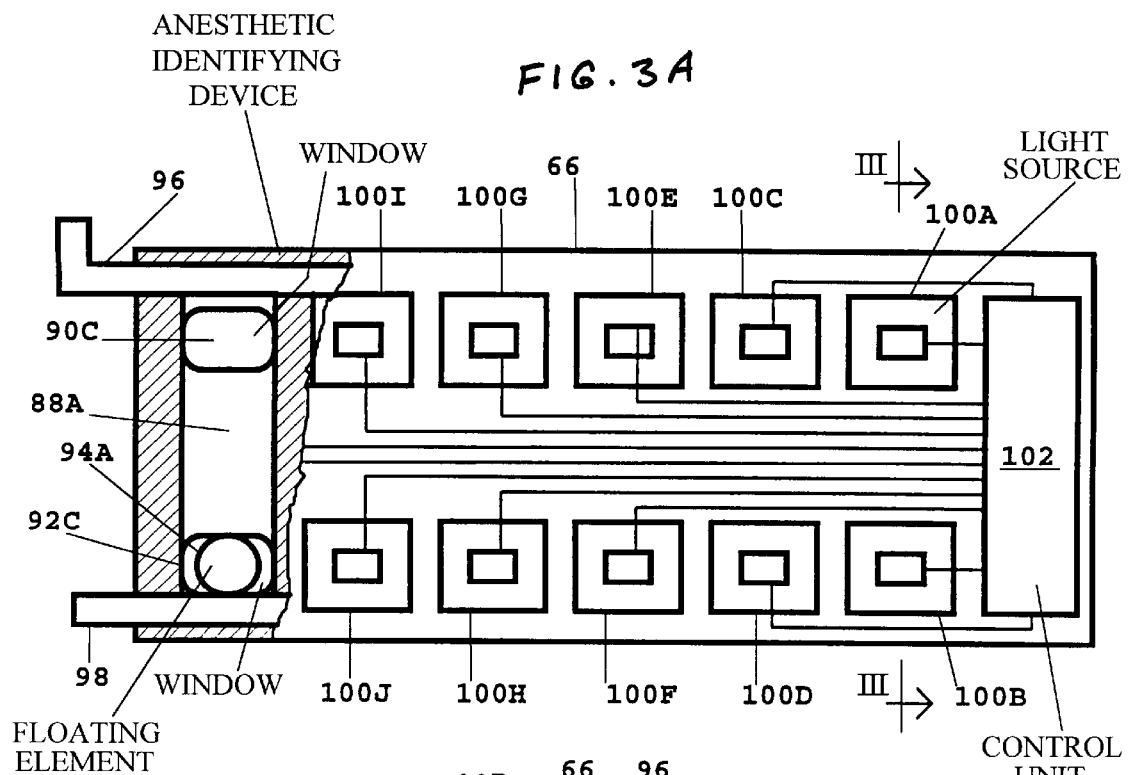
FIGS. 3A and 3B show a second embodiment of an anaesthetic identifying device constructed according to the invention, with FIG. 3B being a sectional view taken along line A—A of FIG. 3A.
Figure 3B:
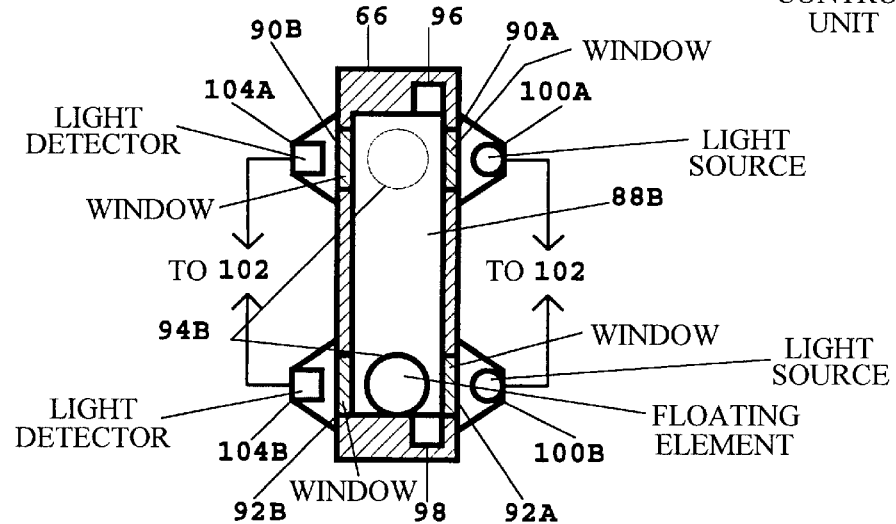

FIGS. 3A and 3B shows a second embodiment of the device 66. The device 66 includes a container with a number of cavities 88A and 88B (only two are shown in FIG. 3). A first window 90A and a second window 90B are arranged opposite each other in the upper part of the cavity 88B. (Only one window 90C is shown in the upper part of cavity 88A.) A third window 92A and a fourth window 92B are arranged opposite each other in the lower part of the cavity 88B. (Only one window 92C is shown in the lower part of cavity 88A.) The cavities 88A and 88B are filled with anaesthetic fluid, and a floating element 94A, 94B is arranged in each cavity 88A and 88B. The density of the floating elements 94A and 94B is devised so the elements either float or sink, depending on the density of the anaesthetic at a specific temperature. The floating element 94A can be devised to float in an anaesthetic fluid while the floating element 94B simultaneously sinks in that fluid. (Here, one such specific floating element is placed in each cavity in the device 66.)

The device 66 can be filled with anaesthetic fluid from a container (not shown) in the anaesthetic vaporizer 6. Influx is via an inflow tube 96 which is connected to all the cavities 88A and 88B. The anaesthetic fluid in the cavities 88A and 88B can be emptied through a drainage tube 98 which is connected to all the cavities 88A and 88B. In principle, the device 66 can also consist of the container in the anaesthetic vaporizer 6. In the latter instance, the inflow tube 96 is a filling tube for the anaesthetic vaporizer 6, and anaesthetic fluid is carried to the vaporizer through the drainage tube 98.

A first light source 100A is arranged at the first window 90A to beam light through the first window 90A to the second window 90B. A second light source 100B is arranged at the third window 92A to beam light through the third window 92A to the fourth window 92B. Light sources 100C–100J are also arranged by the other cavities. The light sources 100A–100J are controlled by a control unit 102.

In the corresponding manner, a first light detector 104A is arranged at the second window 90B to sense light emitted by the first light source 100A, and a second light detector 104B is arranged at the fourth window 94B to sense light emitted by the second light source 100B. (This applies to all the cavities.) The light detectors 104A, 104B send a signal to the control unit 102 when they detect light. The control unit 102 then identifies the anaesthetic fluid from the signals received from the light detectors 100A, 100B.

The function of the device 66 is explained most simply if the cavity 88B is considered (shown in section in FIG. 3B). Depending on the anaesthetic fluid filling the cavity 88B, the floating element 94B will float, thereby blocking light from the first light source 100A, or sink, thereby blocking light from the second light source 100B. So the control unit 102 receives either a signal from the first light detector 104A or from the second light detector 104B. The floating element 94A in the cavity 88A is devised for another density and could e.g. sink, while the floating element 94B floats (indicated with a dashed floating body). Thus, another signal combination can be received from the light detectors by the cavity 88A. When a number of cavities are placed parallel to each other in the device 66, a unique sequence of signals is generated for each anaesthetic fluid. This fluid can then be identified unambiguously.

In the same way as in the previous embodiment, a mixture of anaesthetics causes the density to change. A new, unique signal combination is then generated by the light detectors. Even if the two mixed anaesthetic fluids cannot be identified unambiguously in this situation, the circumstance that two anaesthetic fluids have mixed can be determined. Knowledge that two anaesthetics have been mixed is sufficient to keep the patient from being administered a mixture of the two anaesthetic fluids.

Since a similar effect may occur if the temperature of the anaesthetic fluid changes (e.g. when filling is with an anaesthetic fluid at another temperature), active regulation of the anaesthetic fluid's temperature in the device 66 is appropriate.

Alternatively, a thermometer can be placed in the device to measure the temperature, and a number of cavities 88 can be arranged with floating bodies 94 whose density is devised for one anaesthetic fluid at different temperatures (e.g. 18° C. and 22° C.).

An additional control can be added to the device 66 by including one floating element which sinks and one which floats, irrespective of the anaesthetic fluid filling the cavity 88. This would ensure that the device 66 does not contain any fluid with a density less than the lowest density for an anaesthetic fluid or a density greater than the greatest density for an anaesthetic fluid (e.g. with a floating body with a density of 1,400 kg/m$^3$ and a floating body with a density of 1,900 kg/m$^3$.)

Figure 4:
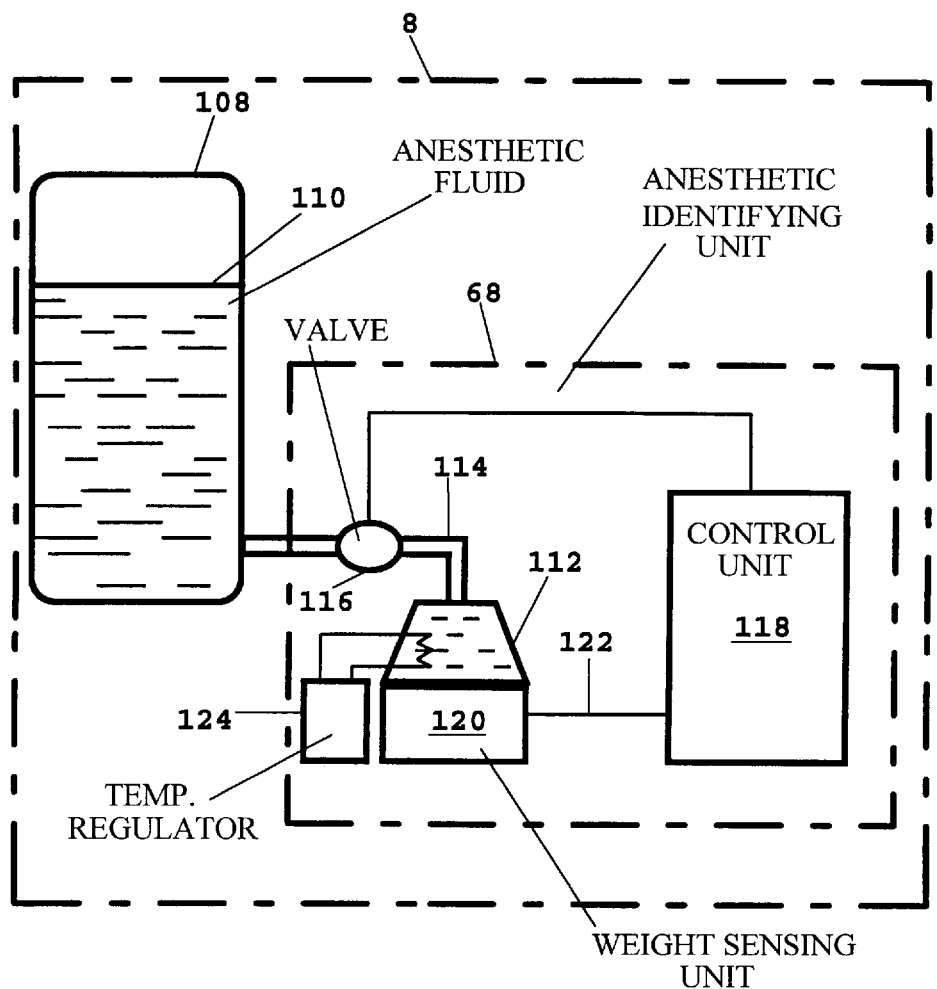
FIG. 4 shows a third embodiment of an anaesthetic identifying device constructed according to the invention.

FIG. 4 shows a third embodiment of the device 68. Anaesthetic fluid 110 is held in a vessel 108 in the anaesthetic vaporizer 8. The anaesthetic fluid 110 can be transferred from this vessel 108 to the device 68 for identification.

The device 68 has a container 112 to which a predetermined amount of anaesthetic fluid 110 can be transferred via a tube 114 and a valve 116. The valve 116 is controlled by a control unit 118. The container 112 is arranged by a weight-sensing unit 120, e.g. a scale. The scale senses the weight, i.e. the mass, of the predetermined amount of anaesthetic fluid 110 in the container 112, and sends measurement results to the control unit 118 via a signal line 122.

The density of the anaesthetic fluid can be determined from the sensed weight, or mass, of the predetermined amount of anaesthetic fluid, and the anaesthetic fluid can be accordingly identified. The control unit 118 can naturally be devised so identification can be made directly, without any need for conversion to density.

A temperature regulator 124 regulates the temperature of anaesthetic fluid in the container 112.

Other ways to weigh, or determine, the weight of the anaesthetic fluid can also be used. It is not even necessary to determine the absolute mass, or weight. Determining the relative deviation is sufficient. In this instance, comparative measurement can be made with a predetermined amount of e.g. water at a predetermined temperature. Piezoelectric elements or the like can also be used for indirect sensing of differences in mass.

Determination of density can also be combined with determination of some other physical property, such as thermal conductivity, thermal absorption, and thermal dielectric constant. This would facilitate identification, especially of anaesthetics with the smallest differences in density.

Figure 5:
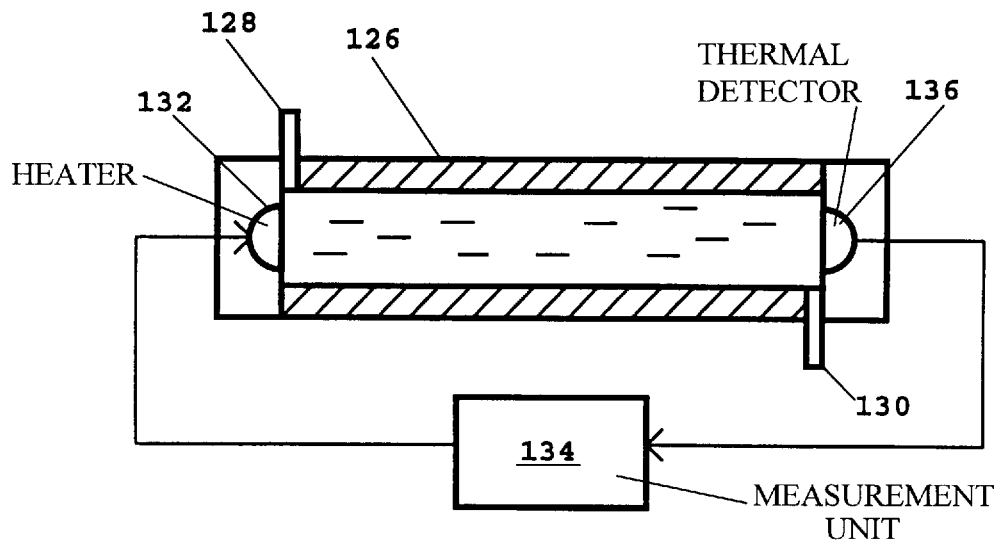
FIG. 5 shows a fourth embodiment of an anaesthetic identifying device constructed according to the invention.

Thermal conductivity can be determined by enclosing a quantity of fluid in e.g. a thermally insulated tube 126, as shown in FIG. 5. The fluid can enter the tube 126 via a fluid entrance 128 and leave the tube 126 via drain 130. On one end of the tube 126, a heater 132 is in contact with the fluid. On the other end of the tube 126, a thermal detector 136 (thermometer or the like) is in contact with the fluid. A control unit is connected to the heater 132 for controlling the release of heat and to the thermal detector 136 for determining the thermal conductivity of the fluid. An exact amount of heat is added by the heater 132 at one end of the tube 126 and the time it takes for a predetermined increase in temperature to be sensed by the thermal detector 136 at the other end of the tube 126 is measured in a measurement unit 134. Differences in thermal conductivity for the different anaesthetic fluids thus make it possible to identify the anaesthetic used.

Other physiological property of the fluid, such as thermal absorption and thermal dielectric constant can be determined with great accuracy by a calorimeter. Since calorimeters are known, it is not necessary to describe them further.

Figure 6:
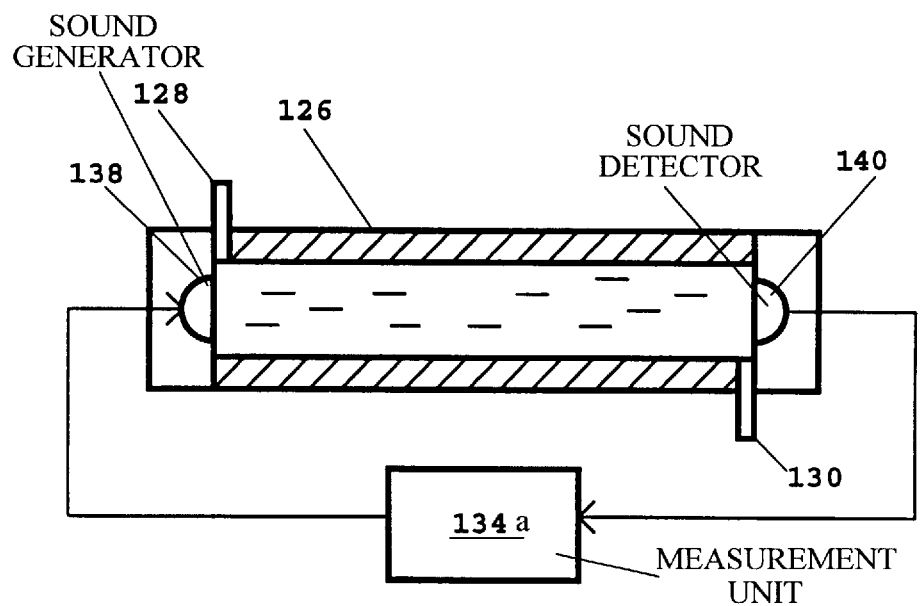
FIG. 6 shows a fifth embodiment of an anaesthetic identifying device constructed according to the invention.

FIG. 6 illustrates a further embodiment. Instead of using a heater 132 and thermal detector 132, as described above, a sound generator 138 and sound detector 140 are utilized instead. The propagation velocity of sound through the fluid is determined in the measurement unit 134*a*. A sound pulse can be allowed to reflect several times for increasing the measured propagation length. Pulses could be emitted with different frequencies for further increasing the accuracy of determination. The sound propagation could also be measured at different temperatures.

Instead of sound propagation velocity, the frequency can be varied in order to find standing sound waves, the frequencies of which can be used for establishing the identity of the anaesthetic fluid.

Determination of the physiological property for the anaesthetic fluid can be combined with measurement of a known concentration (such as optical absorption or measurement of crystal frequency), determination of changes in state (transitions from different states of aggregation) or other physiological properties in order to further increase the possibility of reliable identification.

In the embodiment in FIG. 1, the devices 64, 66 and 68 are each part of anaesthetic system 2 with three anaesthetic vaporizers 4, 6 and 8 and a re-breathing circuit 10 for the patient 12. The device according to the invention can advantageously be used with all kinds of anaesthetic system, regardless of the number of anaesthetic vaporizers or the respiratory circuit employed for the patient.

Although modifications and changes may be suggested by those skilled in the art, it is the intention of the inventor to embody within the patent warranted hereon all changes and modifications as reasonably and properly come within the scope of his contribution to the art.

I claim as my invention:

1. A device for use with an anaesthetic system for identifying at least one anaesthetic, said device comprising:
   a container fillable with an anaesthetic in liquid form; and
   measurement means for interacting with said liquid anaesthetic for identifying at least one parameter related to at least one physical property of said liquid anaesthetic selected from the group of physical properties comprising density, thermal conductivity and thermal absorption for identifying said liquid anaesthetic from said at least one parameter.

2. A device as claimed in claim 1 wherein said measurement means comprises:
   means for identifying a temperature of said liquid anaesthetic; and
   density-sensitive means for determining a parameter related to the density of said liquid anaesthetic at said temperature of said anaesthetic fluid.

3. A device as claimed in claim 2 wherein said density-sensitive means comprises a floating body immersible in said liquid anaesthetic in said container, said floating body comprising means for sinking to a specific depth below a surface of said liquid anaesthetic in said container dependent on the density of said liquid anaesthetic at said temperature of said liquid anaesthetic.

4. A device as claimed in claim 3 wherein said floating body comprises means for settling in said liquid anaesthetic in said container in a position with a predetermined side facing upwardly, and said floating body having a measuring stick disposed thereon at said predetermined side, said measuring stick having gradations thereon respectively identifying different liquid anaesthetics dependent on which gradation is level with a surface of said liquid anaesthetic in said container.

5. A device as claimed in claim 4 wherein said floating body comprises at least two floating elements disposed at a predetermined distance from each other on said measuring stick.

6. A device as claimed in claim 2 wherein said density-sensitive means comprises a plurality of floating elements disposed in said liquid anaesthetic in said container equal in number to a plurality of anaesthetics to be identified, each floating element having a density equal to a density of a respective one of said plurality of anaesthetics to be identified and said floating elements floating or sinking in said liquid anaesthetic in said container dependent on the identity of the liquid anaesthetic in said container.

7. A device as claimed in claim 6 wherein said container comprises a plurality of cylindrical cavities equal in number to said plurality of floating elements and each cavity having one of said floating elements therein and each cylindrical cavity being filled with said liquid anaesthetic, each cavity having an upper part and a lower part with a first pair of transparent windows disposed on the opposite sides of said upper part and a second pair of transparent windows disposed at opposite sides of said lower part and the floating element in each cavity being disposed either in said upper part or said lower part dependent on the identity of said liquid anaesthetic, means for transmitting a light beam through each of said first and second pairs of windows of each cavity, means for detecting said light beam from each of said first and second pairs of windows in each of said cavities and for generating a detector signal, the floating element in each cavity either admitting or blocking said light beam through one of said pairs of windows of each cavity dependent on the identity of said liquid anaesthetic, and means supplied with said detector signals for identifying said anaesthetic dependent upon passage of light through each of said pairs of windows of each of said cavities.

8. A device as claimed in claim 2 wherein said container is fillable with a predetermined amount of said liquid anaesthetic, and wherein said density-sensitive means comprises a weight-sensing element connected to said container for sensing a weight of said container filled with said liquid anaesthetic, and wherein said measurement means comprises means for identifying said liquid anaesthetic in said container from the weight sensed by said weight-sensing element.

9. A device as claimed in claim 1 wherein said measurement means comprises a thermally insulated tube in fluid communication with said container and having said liquid anaesthetic therein, a heater disposed at a first end of said tube for heating said liquid anaesthetic in said tube, a thermal detector disposed at a second end of said tube for measuring changes in the temperature of said liquid anaesthetic in said tube, and means for determining the thermal conductivity of said liquid anaesthetic from said changes in temperature and for identifying said liquid anaesthetic from said thermal conductivity.

10. A device as claimed in claim 1 further comprising thermostat means for regulating a temperature of said liquid anaesthetic in said container for maintaining said anaesthetic fluid at a constant, predetermined temperature.

11. A method for use in an anaesthetic system for identifying at least one anaesthetic, said method comprising the steps of:

(a) filling a container with an anaesthetic in liquid form; and (b) identifying at least one parameter related to at least one physical property of said liquid anaesthetic selected from the group of physical properties comprising density, thermal conductivity and thermal absorption, and identifying said liquid anaesthetic from said at least one parameter.

12. A method as claimed in claim 11 wherein step (b) comprises:

identifying a temperature of said liquid anaesthetic; and determining a parameter related to the density of said liquid anaesthetic at said temperature of said liquid anaesthetic.

13. A method as claimed in claim 11 wherein step (a) comprises filling said container with a predetermined amount of said liquid anaesthetic, and wherein step (b) comprises sensing a weight of said container filled with said liquid anaesthetic, and identifying said liquid anaesthetic in said container from said weight.

14. A method as claimed in claim 11 wherein step (a) comprises connecting a thermally insulated tube in fluid communication with said container and filling said tube with said liquid anaesthetic, and wherein step (b) comprises heating said liquid anaesthetic in said tube from a heat source at a first end of said tube, for measuring changes in the temperature of said liquid anaesthetic in said tube at a second end of said tube, and determining the thermal conductivity of said liquid anaesthetic from said changes in temperature and identifying said liquid anaesthetic from said thermal conductivity.

15. A method as claimed in claim 11 further comprising the step of regulating a temperature of said liquid anaesthetic and maintaining said liquid anaesthetic in said container at a constant, predetermined temperature.

\* \* \* \* \*